United States Patent
Nguyen et al.

(10) Patent No.: US 11,406,727 B2
(45) Date of Patent: Aug. 9, 2022

(54) ENDOSCOPE REPROCESSOR

(71) Applicant: ASP Global Manufacturing GmbH, Shaffhausen (CH)

(72) Inventors: Nick Ngoc Nguyen, Silverado, CA (US); Samuel J. Rhodes, Los Angeles, CA (US); Darius D. Eghbal, Sierra Madre, CA (US)

(73) Assignee: ASP GLOBAL MANUFACTURING GMBH, Schaffhausen (CH)

(*) Notice: Subject to any disclaimer, the term of this patent is extended or adjusted under 35 U.S.C. 154(b) by 436 days.

(21) Appl. No.: 16/446,903

(22) Filed: Jun. 20, 2019

(65) Prior Publication Data

US 2019/0388573 A1 Dec. 26, 2019

(51) Int. Cl.
| | | |
|---|---|---|
| *A61L 2/00* | (2006.01) | |
| *A61L 9/00* | (2006.01) | |
| *A61L 2/18* | (2006.01) | |
| *A61B 90/70* | (2016.01) | |
| *A61L 2/26* | (2006.01) | |
| *B08B 3/02* | (2006.01) | |
| *B08B 3/08* | (2006.01) | |

(52) U.S. Cl.
CPC ............... *A61L 2/18* (2013.01); *A61B 90/70* (2016.02); *A61L 2/26* (2013.01); *B08B 3/02* (2013.01); *B08B 3/08* (2013.01); *A61B 2090/701* (2016.02); *A61L 2202/15* (2013.01); *A61L 2202/24* (2013.01)

(58) Field of Classification Search
CPC . A61L 2/00; A61L 2/0088; A61L 2/18; A61L 2202/24

USPC .................. 422/28, 32, 292, 300–301
See application file for complete search history.

(56) References Cited

U.S. PATENT DOCUMENTS

| | | | |
|---|---|---|---|
| 4,064,886 A | 12/1977 | Heckele | |
| 4,288,882 A | 9/1981 | Takeuchi | |
| 5,279,317 A | 1/1994 | Bowman et al. | |
| 5,288,467 A | 2/1994 | Biermaier | |
| 5,308,406 A | 5/1994 | Wallock et al. | |
| 5,320,119 A | 6/1994 | Griffiths | |
| 5,471,706 A | 12/1995 | Wallock et al. | |
| 5,511,568 A | 4/1996 | Bowman et al. | |
| 8,118,042 B2 | 2/2012 | Ngo et al. | |
| 9,060,804 B2 | 6/2015 | Meyer | |
| 9,132,456 B2 | 9/2015 | Kawai et al. | |
| 9,144,469 B1 | 9/2015 | Geddis et al. | |

(Continued)

FOREIGN PATENT DOCUMENTS

WO 98/29028 A1 7/1998

OTHER PUBLICATIONS

PCT International Search Report PCT/IB2019/055218 dated Sep. 25, 2019, 4 pages.

(Continued)

*Primary Examiner* — Monzer R Chorbaji
(74) *Attorney, Agent, or Firm* — Etan S. Chatlynne; Roberts Calderon Safran & Cole P.C.

(57) ABSTRACT

An endoscope reprocessor having a tube and nozzles may be used to increase the effectiveness of an endoscope reprocessor. Fluid may be delivered into the tube through the nozzle, which may be oriented in various orientations. Energy of the flow within the tube may be increased by introduction of fluid through the nozzles, which may additionally move the endoscope within the tube.

22 Claims, 8 Drawing Sheets

(56) References Cited

U.S. PATENT DOCUMENTS

| | | |
|---|---|---|
| 9,216,074 B2 | 12/2015 | Vedovelli |
| 2002/0017316 A1* | 2/2002 | Ochiai .................. A61B 1/123 |
| | | 134/102.1 |
| 2004/0118440 A1 | 6/2004 | Sasaki et al. |
| 2006/0193760 A1 | 8/2006 | Hight, III |
| 2015/0359599 A1 | 12/2015 | Fagan et al. |

OTHER PUBLICATIONS

Chad Terhune, "Superbug outbreak: UCLA will test new scope-cleaning machine," LA Times, Jul. 22, 2015, http://www.latimes.com/business/la-fi-ucla-superbug-scope-testing-20150722-story.html, pp. 1-4.

* cited by examiner

ENDOSCOPE REPROCESSOR

CROSS-REFERENCE TO RELATED APPLICATION

The present application claims priority under 35 U.S.C. § 119 to U.S. Provisional Patent Application No. 62/687,689, filed Jun. 20, 2018. The entire contents of this application is incorporated by reference herein in its entirety.

FIELD

The subject matter disclosed herein relates to disinfecting endoscopes.

BACKGROUND

Endoscopes are reusable medical devices. An endoscope should be reprocessed, i.e., decontaminated, between medical procedures in which it is used to avoid causing infection or illness in a subject. Endoscopes are difficult to decontaminate as has been documented in various news stories. See, e.g., Chad Terhune, "Superbug outbreak: UCLA will test new scope-cleaning machine," LA Times, Jul. 22, 2015, http://www.latimes.com/business/la-fi-ucla-superbug-scope-testing-20150722-story.html (last visited Oct. 30, 2017). Typically, endoscope reprocessing is performed by a disinfection procedure that includes at least the following steps: removing foreign material from the endoscope, cleaning the endoscope, and disinfecting the endoscope by, among other things, submerging it in a disinfectant capable of substantially killing microorganisms thereon, e.g., infection causing bacteria. One exemplary disinfectant is CIDEX® OPA Solution, manufactured and distributed by Applicant, Advanced Sterilization Products, Division of Ethicon US, LLC, a Johnson & Johnson company ("ASP").

Endoscope reprocessing may be conducted by a healthcare worker, or with the assistance of machinery, such as an endoscope reprocessor, e.g., ASP's EVOTECH® Endoscope Cleaner and Reprocessor.

SUMMARY OF THE DISCLOSURE

An endoscope reprocessor is disclosed herein. The endoscope reprocessor may include a basin. The basin may include a drain hole. A tube in a coiled configuration may be fluidly coupled to the drain hole. The tube may include an inlet, an outlet, a wall having an outer surface, and a nozzle. The tube may define a curvilinear axis therethrough.

The nozzle may include an ingress and a base disposed on the outer surface of the tube between the inlet and the outlet. The nozzle may also include a hose barb disposed proximate to the ingress. Fluid may be delivered into the tube through the nozzle. The nozzle may be oriented in various orientations. For example, in spherical coordinates, the nozzle may be oriented with a first polar angle of between approximately zero degrees and approximately ninety degrees from a first reference line that extends perpendicularly from the curvilinear axis and through the base of the nozzle. The polar angle may be approximately zero degrees. Further, the nozzle may be oriented with a first azimuthal angle of between approximately zero degrees and approximately ninety degrees about the first reference line. The first azimuthal angle may be approximately thirty degrees. The nozzle may be oriented at various other orientations, e.g., the first polar angle may be approximately forty-five degrees and the first azimuthal angle may be approximately forty-five degrees.

The tube may be comprised of various segments connected via connector components. The connector components may include a nozzle. For example, the tube may comprise a first tube segment connected to a second tube segment by a connector component including the nozzle. Further, the connector component may comprise a hollow-wall structure having an outer connector surface and an inner connector surface including a plurality of ports disposed therethrough. The plurality of ports may each have a central axis that is perpendicular to an egress of the port. A hollow may be disposed between the inner connector surface and the outer connector surface such that fluid may be provided into the tube along a fluid path including the ingress of the nozzle, the hollow, and the port. At least one of the plurality of ports may be oriented such that a second polar angle between the central axis of that port and a second reference line that is perpendicular to the curvilinear axis and passes through the port is between about zero degrees and about forty-five degrees.

Also disclosed herein is a method of using an endo scope reprocessor that includes such a tube. An insertion tube of an endoscope, likely in a contaminated state, may be inserted through the tube. Fluid, e.g., a disinfectant, may be delivered through the nozzle while the same or a different fluid is delivered through the tube's inlet. The insertion tube may be floated within the tube by forces exerted by the fluid flowing through the nozzles. The fluid may be provided through the nozzles at a varying flow rate. Thus, the insertion tube may be moved in response to changing forces depending on the flow rate of the fluid. The insertion tube may be removed from the endoscope reprocessor in a disinfected state.

Further modifications to an endoscope reprocessor are disclosed herein. A bracket may be disposed in a basin. The bracket may include an inlet and a plurality of jets, e.g., between two and ten, e.g., three, directed toward one or more focal points. The bracket may be connected to a manifold having a plurality of outlets, e.g., two, three, four, or five. The manifold may be connected to a source of disinfectant fluid. The bracket may also include a clamp. An endoscope may be disposed within the endoscope reprocessor, with the tip of the insertion tube supported by the clamp. The endoscope may include an elevator at the distal end of the elevator channel, i.e., within the tip of the insertion tube. The tip and the elevator may be positioned at the focal point or points, supported by the clamp.

A wire frame may also be provided in the endoscope reprocessor. The bracket and manifold may be attached to the wire frame.

As used herein, the term "curvilinear axis" may be understood to indicate a longitudinal axis of an object that has been configured to have a curved shape. Specifically, a straight tube that has a longitudinal axis may be configured into a coiled shape such that the longitudinal axis becomes a curvilinear axis.

As used herein, the terms "polar angle" and "azimuthal angle" may be understood to indicate polar and azimuthal angles of a spherical-coordinate system.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like first reference numerals identify the same elements and in which:

MODES OF CARRYING OUT THE INVENTION

The following detailed description should be read with first reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Figure 1:
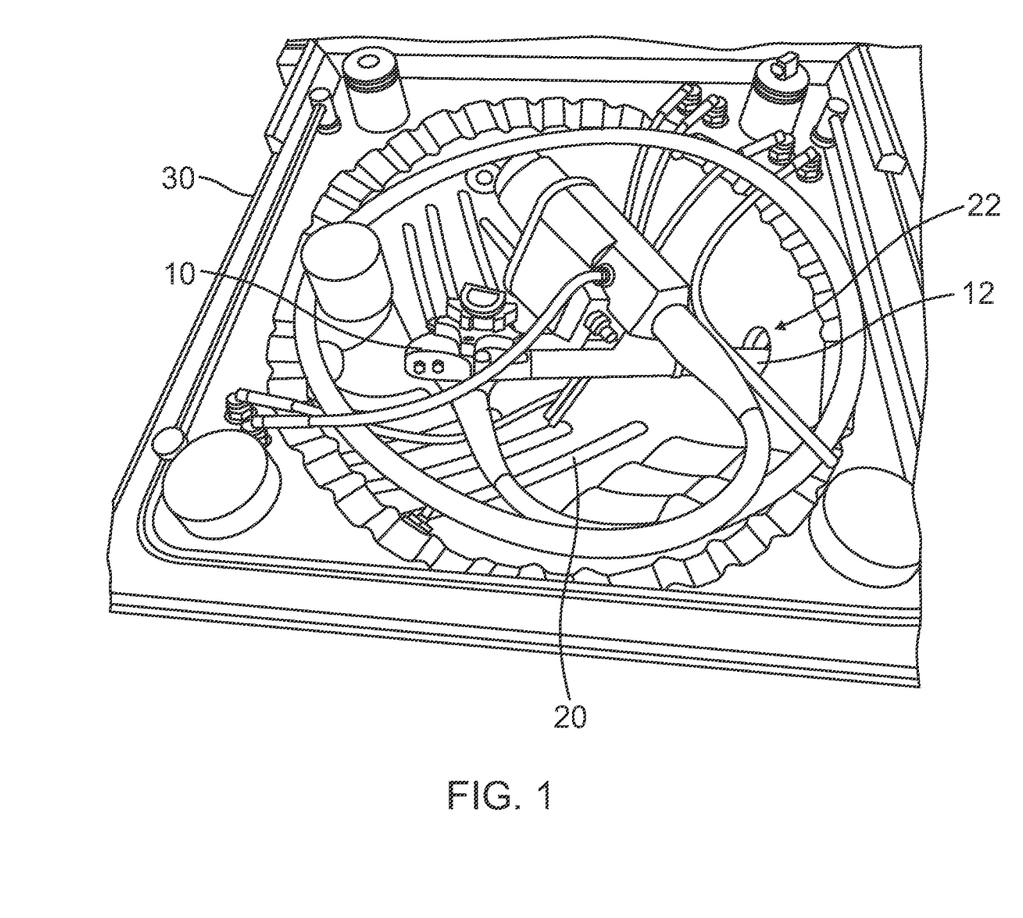
FIG. 1 depicts an endoscope in a basin of an endoscope reprocessor.

FIG. 1 reflects an endoscope 10 disposed within a basin 20 of an endoscope reprocessor 30. Basin 20 includes a drain hole 22. Insertion tube 12 of endoscope 10 exits basin 20 via drain hole 22.

Figure 2:
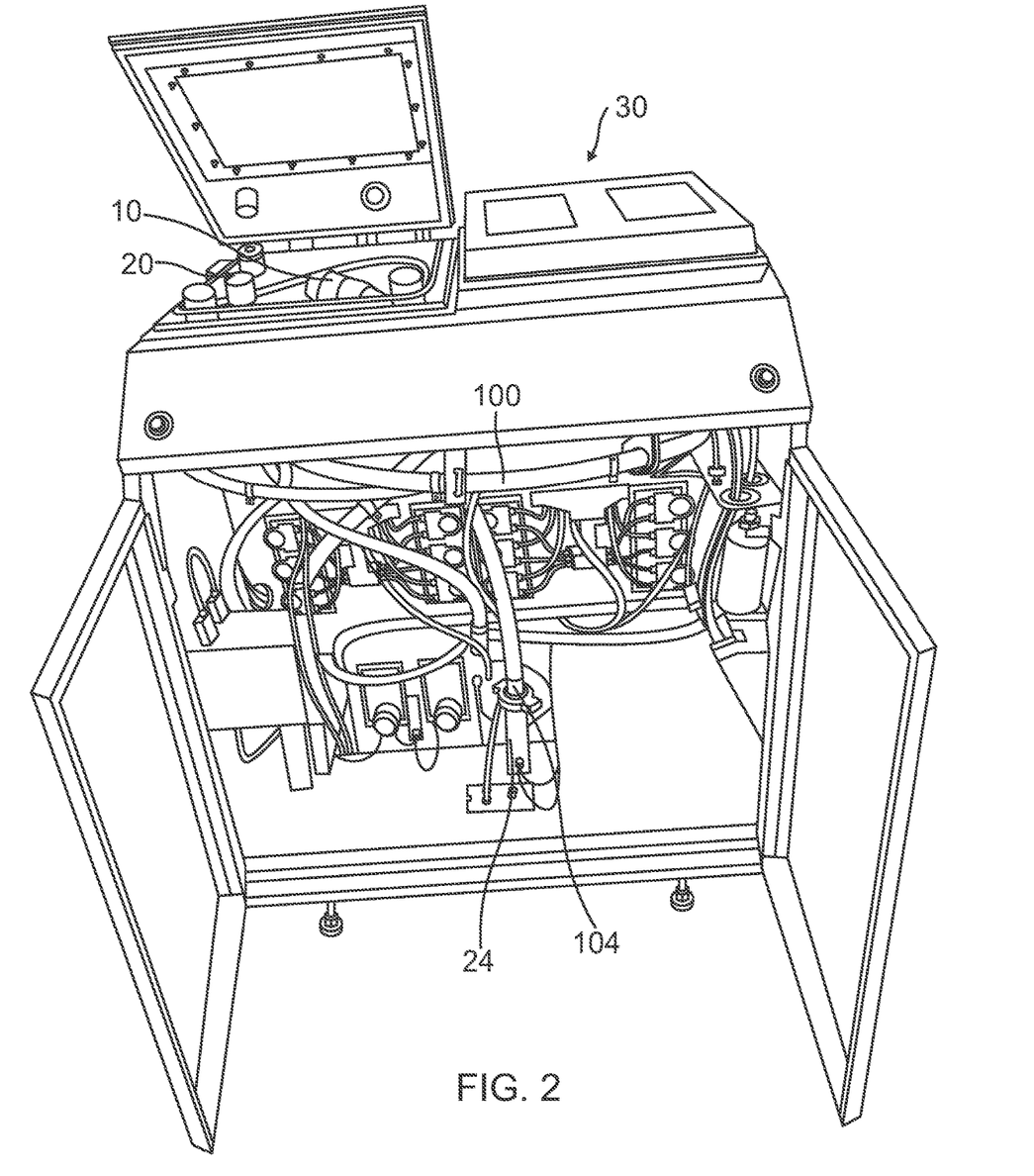
FIG. 2 depicts the endoscope reprocessor of the basin depicted in FIG. 1.
Figure 3:
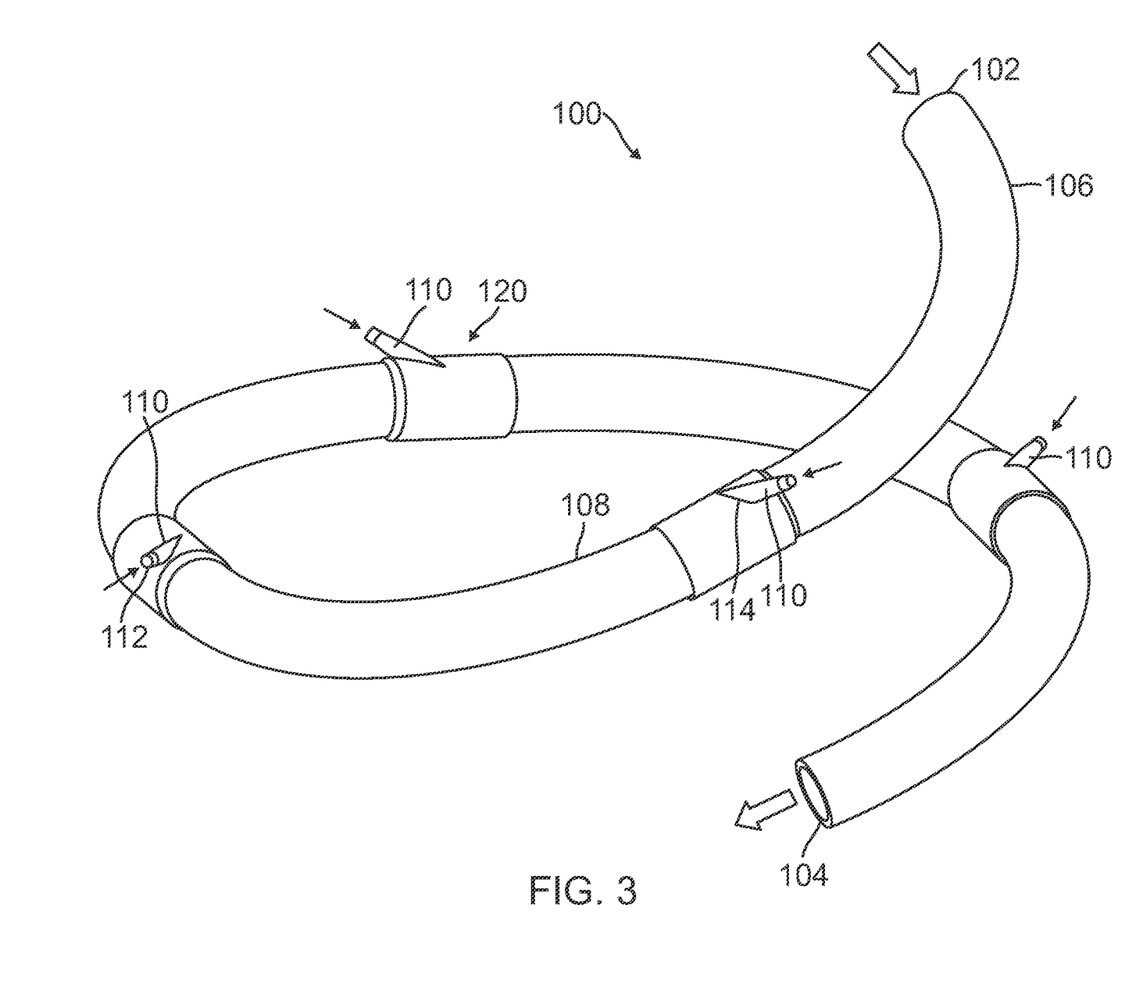
FIG. 3 depicts a coiled tube of the endoscope reprocessor of FIG. 2.

FIG. 2 reflects endoscope reprocessor 30, which contains at least one coiled tube 100 (i.e., a tube in a coiled configuration), further detailed in FIG. 3. Tube 100 includes an inlet 102 fluidly coupled to drain hole 22 and an outlet 104 fluidly coupled to a pump 24. Tube 100 further includes a wall with an inner surface and an outer surface. Because inlet 102 is coupled to drain hole 22, and insertion tube 12 exits basin 20 via drain hole 22, insertion tube 12 thus extends through the inside of coiled tube 100 and rests against the coiled tube's inner surface.

Thus, fluid, e.g., a disinfectant, such as CIDEX® OPA Solution, introduced or within basin 20 may flow out of drain hole 22 and through tube 100 to pump 24. Pump 24 may be fluidly coupled to basin 20 such that any fluid it receives may be pumped back up to basin 20 and reintroduced therein. Accordingly, during operation of endoscope reprocessor 30, the fluid may be continuously recirculated from basin 20, through tube 100, out of outlet 104, into pump 24, and back up to basin 20. The fluid is thus in continuous contact with insertion tube 12, which assists in disinfecting it.

Disinfectant processes are typically associated with a microbial reductions of $10^{-6}$ (Log 6), as compared to washing (e.g., with soap and water) or sterilization, which are typically associated with microbial reductions of $10^{-3}$ (Log 3) and $10^{-12}$ (Log 12) respectively. Tube 100 may include along its length, between its inlet 102 and outlet 104, a nozzle 110 or a plurality of nozzles 110, which may be useful for increasing the effectiveness of a disinfection process conducted by endoscope reprocessor 30.

Figure 4:
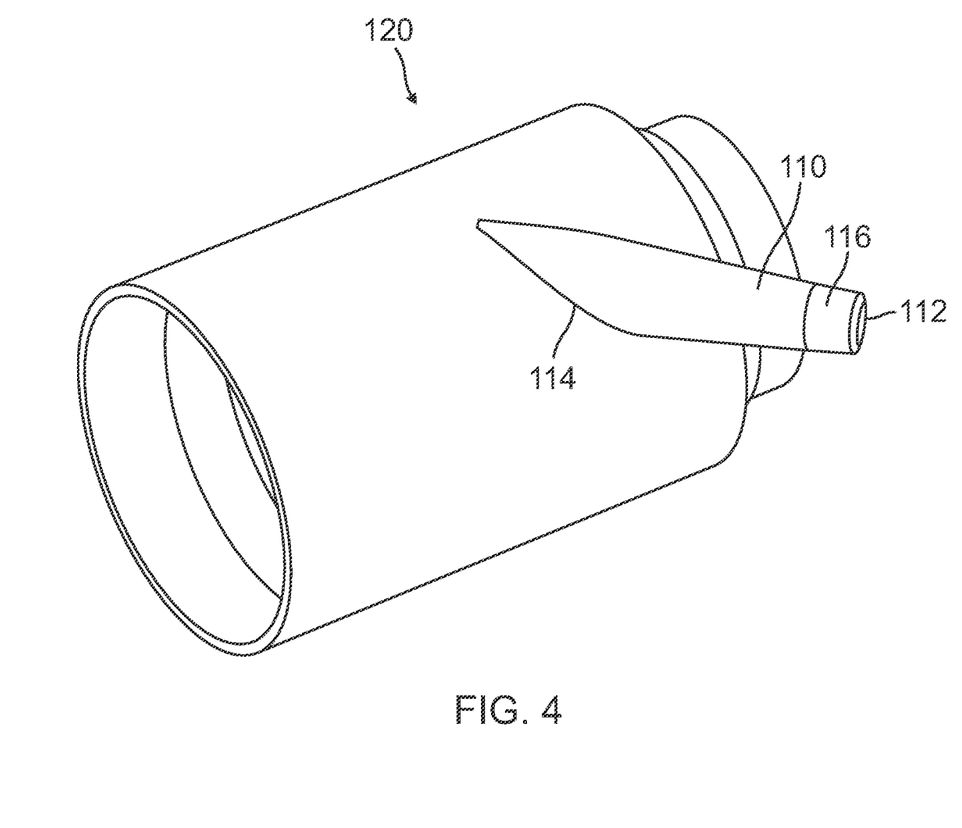
FIG. 4 depicts a connector component of the coiled tube of FIG. 3.

With further reference to FIG. 4, nozzle 110 may include an ingress 112, and a base 114 disposed on the outer surface of tube 100. Nozzle 110 is hollow and provides a path from ingress 112 to the inside of tube 100. As shown, nozzle 110 is provided on a tubing connector component 120 that can connect a first segment 106 of tube 100 to a second segment 108 of tube 100. Connector component 120 may be fabricated from any suitable process, e.g., injection molding, machining, or 3D printing.

Tubing segments 106 and 108 may be connected to connector component 120 by, e.g., a friction fit, snap fit, or press fit connection. Moreover, tube segments 106 and 108 may be rotated circumferentially relative to connector component 120 before or after connection thereto, which may assist in creating coiled tubing of irregular (e.g., non-helical) shapes. Alternatively, the nozzle may be positioned circumferentially with respect to the segments, which may provide various other advantages. For example, if tubing 100 is provided in a helical configuration, e.g., with four connector components, the nozzles may be oriented relative to each other at 0 degrees, 90 degrees, 180 degrees, and 270 degrees. The connections to connector component 120 should be fluid tight to avoid leakage. Accordingly, it may be desired to bond segments 106 and 108 to connector 120 using, e.g., a sealant, solvent, or adhesive.

Fluid may be introduced into coiled tube 100 via nozzles 110 in addition to inlet 102. For example, pump 24, a different pump, or both, may fluidly connect a source of fluid to ingresses 112 of nozzles 110 and pump the fluid therethrough. To assist in any such connections, nozzle 110 may include a tubing connector, e.g., hose barb 116, proximate to ingress 112.

Introduction of fluid through nozzles 110 adds energy to the fluid already flowing within tube 100. This energy may increase vorticity, turbulence, and shear stresses in the flow, which may assist in removing microorganisms or other bioburdens from insertion tube 12. Nozzles 110 may each have the same, similar, or different orientations relative to tube 100. Further, nozzles 110 may be oriented at any angle with respect to tube 100.

Exemplary orientations are provided in spherical coordinates relative to a reference line that is perpendicular to a curvilinear axis of tube 100 and passes through base 114 of nozzle 110. Nozzle 110 may be provided in various orientations relative to tube 100. For example, as shown in FIGS. 3 and 4, nozzle 110 may be oriented such that its polar angle to the reference line is between about thirty and forty-five degrees and its azimuthal angle about that reference line is between about thirty and forty-five degrees. In this orientation, fluid introduced through nozzle 110 may impart a helical flow component around insertion tube 12, aided in part by the arcuate or circular shape of connector 120's inner surface as well as tube 100's inner surface. Helical flow around insertion tube 12 may be accomplished by orienting nozzle 110 over a wide range of polar and azimuthal angles.

Depending on various factors, e.g., the diameter of insertion tube 12, the diameter of coiled tube 100, and removal of bioburdens besides microbes, optimal angles of nozzle 110 may vary. However, it should be understood that the polar angle of nozzle 110 may range from approximately zero to approximately ninety degrees and that the azimuthal angle may also range from approximately zero to approximately ninety degrees. In those instances where the polar angle is between about zero degrees and fifteen degrees from the reference line, fluid introduced through nozzles 110 may impinge directly upon insertion tube 12, which may also assist in removal of bioburdens therefrom. However, there may be a tradeoff between local improvement of cleaning close to the site of impingement and the amount of energy imparted into the fluid for cleaning locations away from the site of impingement.

In typical usage, fluid from basin 20 flows through drain hole 22 at a flow rate of between approximately fifteen liters per minute and approximately twenty-five liters per minute. Thus, fluid flows through tube 100 at approximately the same rate. The volume flow rate through each nozzle 110 may be between approximately 0.8 liters per minute and approximately 1.2 liters per minute. Further, the flow rate through nozzles 110 may be varied, which results in changing the amount of energy carried by fluid introduced therethrough. For example, flow through the nozzles may be cycled on and off. Alternatively, the flow rate may be varied back and forth continuously between two volume flow rates, e.g., between about 0.8 liters per minute and about 1.2 liters per minute over a period of time lasting anywhere between, e.g., about one second and about ten seconds. By changing the flow rate as a function of time in this manner, insertion tube 12 may be agitated within tube 100, which may further assist in removing bioburden therefrom.

Figure 5:
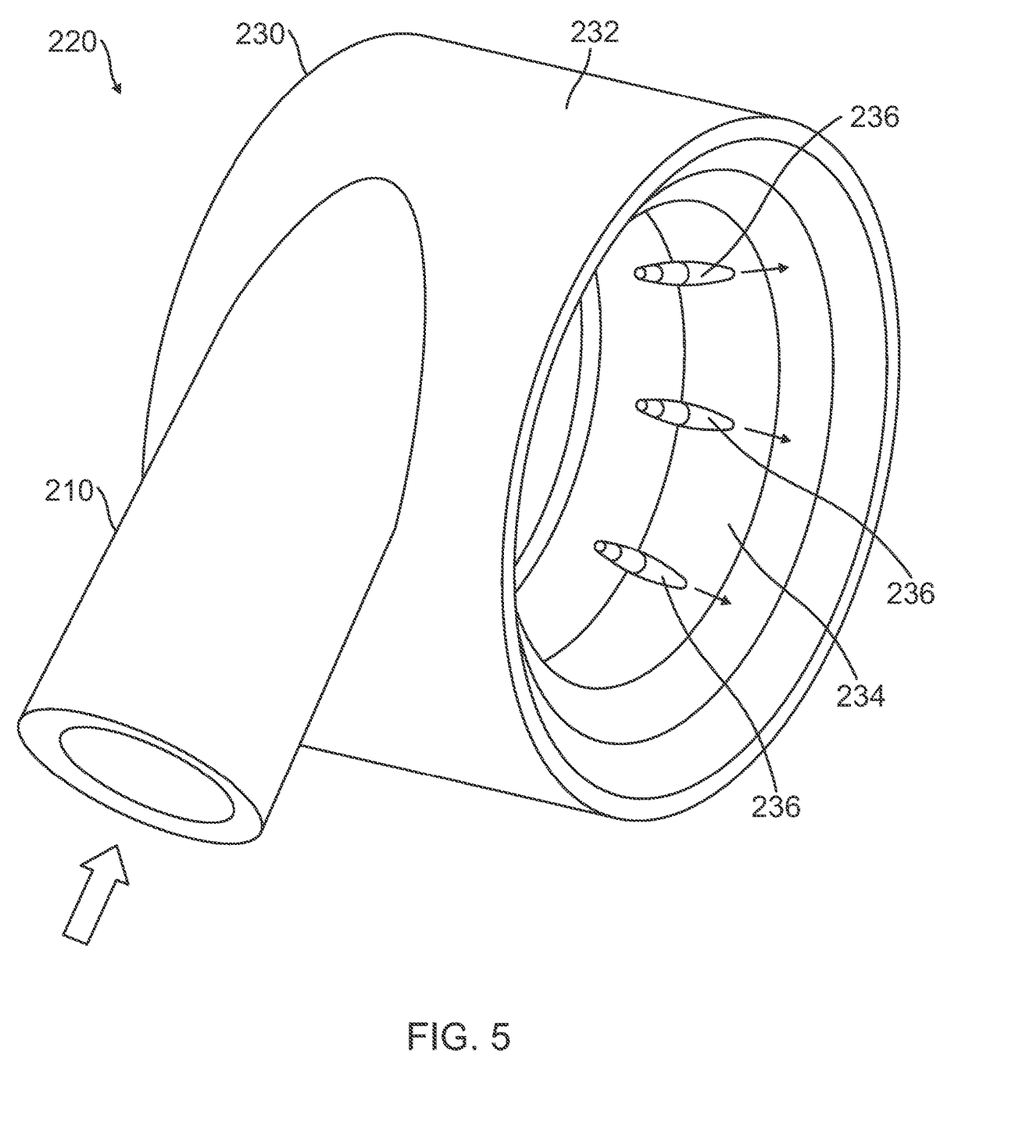
FIG. 5 depicts another embodiment of the coiled tube of FIG. 3.

FIG. 5 reflects a connector 220, which includes a nozzle 210 having a polar angle of about zero degrees and an azimuthal angle of about ninety degrees. Connector 220 may comprise a hollow-wall structure 230. That is, connector 220 may include an outer connector surface 232 and an inner connector surface 234 that define a hollow therebetween. Further, a plurality of ports 236 may be disposed through inner connector surface 234 such that they provide fluid communication from the hollow of connector 220. Accordingly, fluid that enters connector 220 through nozzle 210 flows through the hollow and exits out of ports 236.

The plurality of ports 236 may be provided in various configurations, e.g., spaced circumferentially about the inner surface. At least one of the ports may be oriented such that a polar angle between, first, a second reference line that passes through the port and is perpendicular to a longitudinal axis of connector 220 or the curvilinear axis of tube 100 when connected thereto and, second, a central axis of the port (i.e., a longitudinal axis or an axis that is perpendicular an egress of the port) is between about zero degrees and about forty-five degrees. Thus, flow through the ports may enter connector 220 either transversely to curvilinear axis of tube 100, or with a component of the flow parallel to the curvilinear axis. As with connector 120, introduction of fluid into tube 100 through ports 236 adds energy to the fluid already flowing within tube 100. This energy may increase vorticity, turbulence, and shear stresses in the flow, which may assist in removing microorganisms or other bioburdens from insertion tube 12. Further, in those embodiments where ports 236 are disposed along the bottom of connector 220, e.g., only along the bottom of connector 220, the fluid exiting ports 236 may cause insertion tube 12 to float within tube 100 which may improve flow around the entire surface of insertion tube 12 and thus assist in removing bioburden therefrom.

Figure 6:
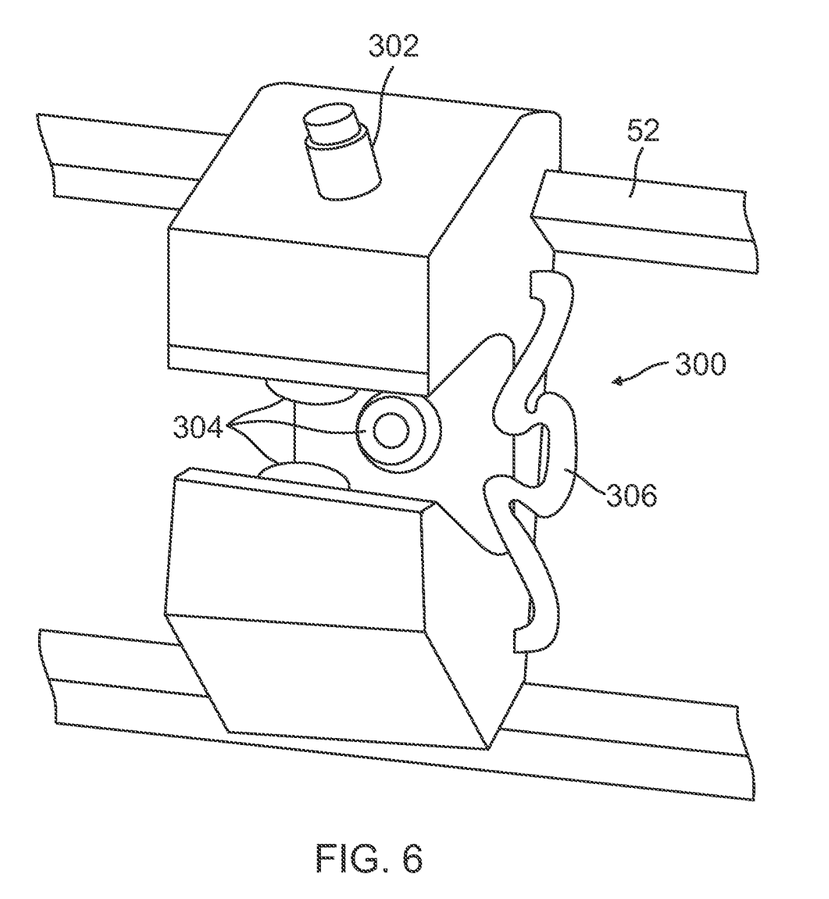
FIG. 6 depicts a bracket for cleaning an endoscope tip in an endoscope reprocessor.
Figure 7:
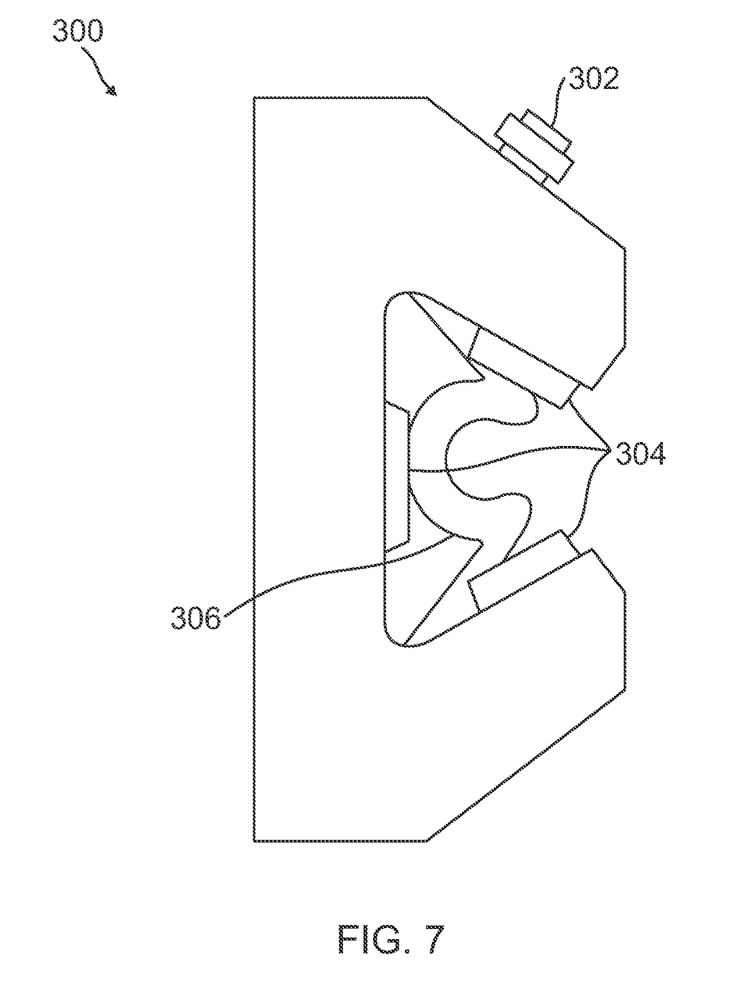
FIG. 7 depicts the bracket of FIG. 6.
Figure 8:
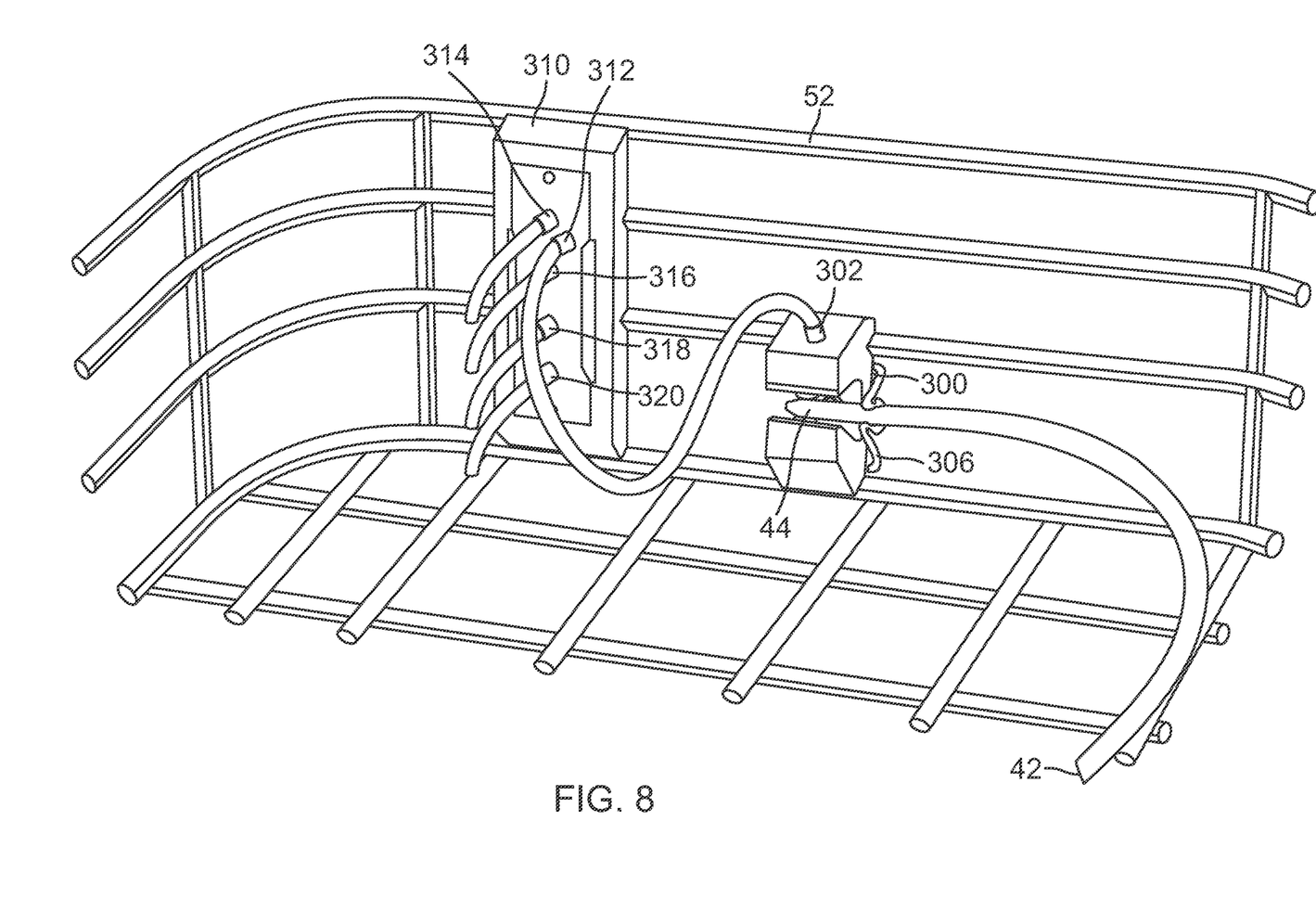
FIG. 8 depicts the bracket of FIG. 6 connected to a manifold.

Further improvements may be made to an endoscope reprocessor that are particularly suitable for cleaning an endoscope that has an insertion tube 42 including an elevator and an elevator channel. The elevator and the portion of the elevator channel proximate thereto are difficult to clean and disinfect. FIGS. 6-8 reflect a bracket 300 that is hollow and includes an inlet 302 and a plurality of outlets or jets 304. It may further optionally include a clamp 306. Bracket 300 may be disposed on wire frame 52, which may be disposed within a basin of an endoscope reprocessor.

Also disposed on wireframe 52 is a manifold 310. As shown, manifold 310 includes five outlets. Outlet 312 connects to inlet 302 on bracket 300. The remaining four outlets 314, 316, 318, and 320, may each be connected to channels of the endoscope. Disinfectant may thus be delivered from the manifold and through the various outlets and tubing connected thereto to the channels of the endoscope and to bracket 300. The disinfectant that reaches bracket 300 may be projected forcefully out of jets 304. As reflected in the figures, jets 304 are each directed to a focal point centered therebetween. The tip 44 of the insertion tube 42, which includes the elevator, may be positioned at that point and may be supported proximate thereto by clamp 306. Thus, jets 306 may forcefully spray tip 44 and the elevator from multiple directions, which assists in removing bioburden therefrom.

As noted, manifold 310 includes five outlets. This manifold is thus designed to be used for disinfecting an endoscope with four channels including an elevator channel. Thus, outlets 314, 316, 318, and 320 are connected to these channels. However, in instances where an endoscope with less than four channels to be disinfected will be reprocessed in the reprocessor, a different manifold with an appropriate number of outlets may be used instead of manifold 310. Manifold 310 may assist a user by reducing the overall number of connections that need to be made between a supply of disinfectant and the endoscope's channels.

By virtue of the embodiments illustrated and described herein, applicant has devised an improved method of disinfecting an endoscope using an endoscope reprocessor. First, an insertion tube (e.g., insertion tube 12) may be positioned through a coiled tube, i.e., a tube in a coiled configuration (e.g., tube 100). The coiled tube may have a curvilinear axis, an inlet, an outlet, a wall with an inner surface and an outer surface, and a nozzle having an ingress and a base disposed on the outer surface between the inlet and the outlet (e.g., nozzles 110 and 210). Second, fluid may be delivered through the nozzle. Fluid may also be delivered through the inlet from the basin of the endoscope reprocessor. In some variations of the method, fluid may be delivered through the inlet of the coiled tube while fluid is also being delivered through the nozzle. Third, the insertion tube may be floated within the fluid such that all of it or portions of it do not contact inner surfaces of the coiled tube. Fourth, the fluid may be provided through the nozzle at a varying flow rate, e.g., by cycling the flow on or off, or oscillating the flow rate between a first flow rate and a second flow rate. Fifth, the insertion tube may be moved or agitated within the coiled tube. In this method, the fluid may be a disinfectant. Accordingly, this method may be used to disinfect an endoscope.

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometries, materials, dimensions, ratios, steps, and the like discussed above are illustrative. Accordingly, the claims should not be limited to the specific details of structure and operation set forth in the written description and drawings.

We claim:

1. An endoscope reprocessor, comprising:
a basin including a drain hole;
a tube in a coiled configuration fluidly coupled to the drain hole, the tube having a curvilinear axis, an inlet, an outlet, a wall including an outer surface, and a nozzle having an ingress and a base disposed on the outer surface between the inlet and the outlet such that a fluid may be delivered into the tube through the nozzle.

2. The endoscope reprocessor of claim 1, wherein the nozzle is oriented with a first polar angle of between approximately zero degrees and approximately ninety degrees from a first reference line that extends perpendicularly from the curvilinear axis and through the base of the nozzle.

3. The endoscope reprocessor of claim 2, wherein the first polar angle is approximately zero degrees.

4. The endoscope reprocessor of claim 2, wherein the nozzle is oriented with a first azimuthal angle of between approximately zero degrees and approximately ninety degrees about the first reference line.

5. The endoscope reprocessor of claim 4, wherein the first azimuthal angle is approximately thirty degrees.

6. The endoscope reprocessor or claim 4, wherein the first polar angle is approximately forty-five degrees and the first azimuthal angle is approximately forty-five degrees.

7. The endoscope reprocessor or claim 2, wherein the nozzle further includes a hose barb disposed proximate to the ingress.

8. The endoscope reprocessor of claim 2, wherein the tube comprises a first tube segment connected to a second tube segment by a connector component including the nozzle.

9. The endoscope reprocessor of claim 8, wherein the connector component comprises a hollow-wall structure having
an outer connector surface,
an inner connector surface including a plurality of ports disposed therethrough, each of the plurality of ports having a central axis that is perpendicular to an egress of the port, and
a hollow disposed between the inner connector surface and the outer connector surface, such that the fluid may be provided along a fluid path including the ingress of the nozzle, the hollow, and the port.

10. The endoscope reprocessor of claim 9, wherein at least one of the plurality of ports is oriented such that a second polar angle between the central axis of that port and a second reference line that is perpendicular to the curvilinear axis and passes through the port is between about zero degrees and about forty-five degrees.

11. A method of using an endoscope reprocessor, comprising:
positioning an insertion tube of an endoscope through a tube in a coiled configuration, the tube having a curvilinear axis, an inlet, an outlet, a wall with an inner surface and an outer surface, and a nozzle having an ingress and a base disposed on the outer surface between the inlet and the outlet; and
delivering fluid through the nozzle.

12. The method of claim 11, further comprising delivering the fluid through the inlet while also delivering the fluid through the nozzle.

13. The method of claim 11, further comprising floating the insertion tube within the fluid.

14. The method of claim 11, further comprising providing the fluid through the nozzle at a varying flow rate.

15. The method of claim 11, further comprising moving the insertion tube using the fluid.

16. The method of claim 11, wherein the fluid is a disinfectant.

17. The method of claim 16, further comprising disinfecting the endoscope.

18. An endoscope reprocessor, comprising:
a bracket disposed in a basin, the bracket including an inlet and a plurality of jets directed toward a focal point; and
a manifold connected to a source of disinfectant and the bracket.

19. The endoscope reprocessor of claim 18, further comprising a clamp connected to the bracket.

20. The endoscope reprocessor of claim 19, further comprising an endoscope disposed therein and supported by the clamp, the endoscope including a tip having an elevator, the tip disposed proximate to the focal point.

21. The endoscope reprocessor of claim 19, further comprising a wire frame upon which are mounted the bracket and the manifold.

22. The endoscope reprocessor of claim 19, wherein the manifold includes at least three outlets and the bracket includes at least three jets.

* * * * *

UNITED STATES PATENT AND TRADEMARK OFFICE
CERTIFICATE OF CORRECTION

| | | |
|---|---|---|
| PATENT NO. | : 11,406,727 B2 | Page 1 of 1 |
| APPLICATION NO. | : 16/446903 | |
| DATED | : August 9, 2022 | |
| INVENTOR(S) | : Nick Ngoc Nguyen, Samuel J. Rhodes and Darius D. Eghbal | |

It is certified that error appears in the above-identified patent and that said Letters Patent is hereby corrected as shown below:

On the Title Page

Insert:
-- Related U.S. Application Data
(63) Provisional application No. 62/687,689, filed June 20, 2018. --

Signed and Sealed this
Fifteenth Day of August, 2023

*Katherine Kelly Vidal*

Katherine Kelly Vidal
*Director of the United States Patent and Trademark Office*